United States Patent
Krans et al.

(10) Patent No.: US 8,482,416 B2
(45) Date of Patent: Jul. 9, 2013

(54) INTERACTIVE BABY FEEDING BOTTLE

(75) Inventors: Martijn Krans, Eindhoven (NL); Ronaldus Maria Aarts, Eindhoven (NL); Mark Thomas Johnson, Eindhoven (NL); Armin Gerhard Kohlrausch, Eindhoven (NL); Nicolle Hanneke van Schijndel, Eindhoven (NL)

(73) Assignee: Koninklijke Philips Electronics N.V., Eindhoven (NL)

( * ) Notice: Subject to any disclaimer, the term of this patent is extended or adjusted under 35 U.S.C. 154(b) by 286 days.

(21) Appl. No.: 12/989,660

(22) PCT Filed: Apr. 22, 2009

(86) PCT No.: PCT/IB2009/051642
§ 371 (c)(1), (2), (4) Date: Oct. 26, 2010

(87) PCT Pub. No.: WO2009/133492
PCT Pub. Date: Nov. 5, 2009

(65) Prior Publication Data
US 2011/0036801 A1 Feb. 17, 2011

(30) Foreign Application Priority Data
Apr. 30, 2008 (EP) .................................. 08103788

(51) Int. Cl.
*G08B 23/00* (2006.01)
*A61J 11/00* (2006.01)

(52) U.S. Cl.
USPC .............. 340/573.1; 340/686.1; 340/692; 340/693.5; 215/11.1

(58) Field of Classification Search
USPC ............... 340/573.1, 686.1, 686.6, 692, 687, 340/691.1, 693.5, 540; 215/11.1
See application file for complete search history.

(56) References Cited

U.S. PATENT DOCUMENTS

| 5,489,893 | A * | 2/1996 | Jo et al. ...................... 340/686.4 |
| 6,104,292 | A * | 8/2000 | Rombom et al. .......... 340/573.1 |
| 2001/0047189 | A1* | 11/2001 | Griffith ......................... 606/234 |
| 2005/0240253 | A1* | 10/2005 | Tyler et al. .................... 607/134 |
| 2006/0061985 | A1 | 3/2006 | Elkins |

FOREIGN PATENT DOCUMENTS

| CA | 2390355 A1 | 1/2004 |
| FR | 2729843 A1 | 8/1996 |
| JP | 2007330654 | 12/2007 |
| KR | 20070037838 A | 4/2007 |

OTHER PUBLICATIONS

Junnila et al: "An EMFi-Film Sensor Based Ballistocardiographic Chair: Performance and Cycle Extraction Method": IEEE Workshop on Signal Processing Systems Design and Implementation (SIPS), November 2005, Issue 2-4, pp. 373-377.

* cited by examiner

*Primary Examiner* — Anh V La

(57) ABSTRACT

An interactive baby bottle has an electronic unit that includes a sensor unit configured to sense the heart beat of a person bottle feeding a baby and an actuator unit configured to transmit the sensed heart beat to the baby.

13 Claims, 4 Drawing Sheets

INTERACTIVE BABY FEEDING BOTTLE

FIELD OF THE INVENTION

The subject matter relates to baby feeding bottles and more specifically to interactive baby feeding bottle that allow a baby to experience a feeling of connectedness with the person feeding the baby.

BACKGROUND OF THE INVENTION

Patent document US2006/0061985 discloses a baby bottle comprising an electronic unit for attachment to the baby bottle wherein the electronic unit is configured to emit both light and sound. A microphone is provided in the electronic unit. Using the microphone a user can record sounds to a memory unit for subsequent playback. The recorded sounds can be played back on a need basis to comfort the baby and give a soothing experience.

The baby bottle disclosed in US2006/0061985 can only comfort the baby. While drinking milk from such a baby bottle, the baby may not experience the connectedness with the person feeding the baby and hence it may be difficult to facilitate the drinking process.

Hence, it would be advantageous to have an improved baby bottle that can create an experience of connectedness between the baby and the person feeding the baby thereby facilitating the drinking process.

SUMMARY OF THE INVENTION

Accordingly, the present subject matter preferably seeks to mitigate, alleviate or eliminate one or more of the above mentioned disadvantages singly or in combination. In particular, it may be seen as an object of the present subject matter to provide a baby bottle that can create an experience of connectedness between the baby and the person feeding the baby.

This object and several other objects are obtained in a first aspect of the present subject matter by providing an interactive baby bottle with an electronic unit comprising:
a sensor unit configured to sense the heart beat of a person bottle feeding a baby; and
an actuator unit configured to transmit the sensed heart beat to the baby.

The sensor unit enables to sense the heart beat of the person (e.g. mother) bottle feeding the baby. The actuator unit enables communication or transmission or transfer of the sensed heart beat to the baby. Due to the feedback of the sensed heart beat to the baby, the baby feels more connected to the person (e.g. mother) bottle feeding the baby.

When mother's breast feed, they create and maintain close contact with their baby. While breast feeding, mother's automatically have eye and skin contact with their baby. At the same time, the baby listens to its mother's heart beat, breathing and familiar soothing voice. A heart beat sound is known to produce a calming and soothing effect on a baby, particularly when it is the mother's identical heart beat which the infant came to know during gestation.

Infants recognize their own mother's heart beat. This sound gives great comfort to a stressed baby only second to the mother's holding and cuddling. Thus, true mother's heart beat sound becomes a very effective way of calming and soothing the baby.

The disclosed interactive baby bottle can facilitate the drinking process since it creates an experience of connectedness between the baby and the person (e.g. mother) bottle feeding the baby thereby approaching breast feeding. Further, the baby can be calmed down by the feeling of connectedness with the feeding person. The disclosed interactive baby bottle can provide comforting interaction between the baby and the person (e.g. mother) bottle feeding the baby.

In an embodiment, the actuator unit is configured to transmit the sensed heart beat of the person (e.g. mother) to the baby in real-time. In order to truly influence the mood-state of the baby by the feeding (e.g. mother) person, the baby needs to get direct feedback on the actual heart beat of the person (e.g. mother) bottle feeding the baby. The disclosed baby bottle is interactive and is provided with an electronic unit that gives real-time feedback to the baby on the actual heart beat. The baby can feel or hear the mother's heart beat and thus can experience a sense of connectedness. Further, the disclosed interactive baby bottle can provide real-time comforting and soothing experience.

The sensed heart beat is fed back to the baby in real-time. The real-time feedback can create a higher level of bonding between the baby and the person (e.g. mother) bottle feeding the baby. This can facilitate the drinking process.

In a further embodiment, the sensor unit comprises one of the following: (photo) plethysmogram PPG on finger or part of the hand or the ear or other body part, SPO2 sensor, electrical electrodes measuring ECG signal, non-galvanic capacitive electrodes, acoustical sensor with microphone and any other heart rate sensor. This has the advantage that the disclosed interactive baby bottle is simple to use. There is no necessity to wear any additional device since the sensor is made available on the baby bottle itself. Further, the person (e.g. mother) bottle feeding the baby can feed the baby in a normal manner and there is no need to change the bottle feeding process.

In a still further embodiment, the actuator unit comprises one of the following:
a plurality of vibration elements configured to generate tactile sensation of the sensed heart beat, the vibration element integrated in a teat or the vibration element disposed suitably on the interactive baby bottle to transmit the sensed heart beat via the teat to the baby
one or more speakers disposed on the interactive baby bottle and configured to provide real-time auditory feedback of the sensed heart beat to the baby.

While mother's breast feed, the baby listens to its mother's heartbeat, breathing and familiar soothing voice. Integrating the vibration element in the teat can generate tactile sensation of the heart beat. The teat is close to the mouth of the baby as is the case during breast feeding where the mouth is close to the breast. The sensed heart beat from the teat can be more effective in creating a sense of connectedness to the person (e.g. mother) bottle feeding the baby.

In a still further embodiment, the interactive baby bottle comprises:
a memory unit configured to store the sensed heart beat; and
a delay unit configured to time-delay the sensed heart beat by a predetermined time period and then transmit the sensed heart beat to the baby. This allows the interactive baby bottle to be designed such that it transmits the heartbeat of the person (e.g. mother) bottle feeding the baby with a certain time delay to the baby. The memory unit can store the heart beat signals from a previous time period. In case the person (e.g. mother) bottle feeding the baby becomes panic or stressed or distracted, undesired signals may be produced. It is not necessary to pass on these undesired signals to the baby. The electronic unit can just repeat the more relaxed heart beat signals from the previous time period that is stored in the memory unit.

In a still further embodiment, the sensor unit is configured to sense at least one body parameter of the person bottle feeding the baby, the at least one body parameter being one of breathing rate, body movement, body temperature, audible sensation, tactile sensation and olfactory sensation. The actuator unit is further configured to transmit the sensed body parameter to the baby.

During breast feeding, the baby can feel or hear the sound of mother's heart beat or breathing rate. Further, the baby can also sense the body temperature, olfactory and tactile related sensory signals (e.g. scent) which can give a soothing and comforting experience to the baby. The disclosed interactive baby bottle can be provided with sensors to sense the body temperature, olfactory, tactile related sensory signals of the person (e.g. mother) bottle feeding the baby. The actuator can transmit the sensed sensory signals to the baby thereby strengthening the bond between the baby and the person bottle feeding (e.g. mother) the baby. Further, it can also facilitate the drinking process and create a natural feeling. The natural feeling can result in the baby being both physically and mentally being closely connected to the person (e.g. mother) bottle feeding the baby.

In some embodiments, the sensor unit configured to sense the breathing rate comprises one of:
- motion sensors disposed on chest or belly of the person bottle feeding the baby
- stretch sensors configured to measure volume variations, the stretch sensor being disposed on chest or belly of the person bottle feeding the baby
- Ballistocardiogram
- Phonocardiogram Phonocardiogram is the measurement of the heartbeat with a microphone (e.g. a stethoscope with a microphone). Ballistocardiogram is the measurement of the heartbeat by measuring the movement of the whole body (which vibrates to the arterial arch impulse) the principles of which are disclosed in the paper "An EMFi-film sensor based ballistocardiographic chair performance and cycle extraction method", Junnila, S et.al, IEEE Workshop on Signal Processing Systems Design and Implementation, 2005, Volume, issue 2-4, pp. 373-377, Nov. 2005.

In a still further embodiment, the interactive baby bottle comprises a wirelessly rechargeable battery. Wirelessly charging the battery has several benefits such as better portability, lower cost, no necessity of carrying a charger. It is also possible to provide one or more batteries to provide power to the sensor and actuator unit. All the components may be powered from single battery or different batteries may be included for powering one or more separate components.

In a still further embodiment, the electronic unit is integrated into the interactive baby bottle. Integrating the electronic unit into the bottle makes the interactive baby bottles a single piece apparatus which is convenient to carry and use. It is also possible to dispose the electronic unit on any convenient position on the interactive baby bottle. To this end, the electronic unit can be provided with a structure that allows it to be attached in various positions. As an illustrative example, the electronic unit can be screwed (or fixed using Velcro material) onto the interactive baby bottle. In such a case a wireless interface is needed for communication with the interactive baby bottle.

In a still further embodiment, the electronic unit is integrated into the interactive baby bottle covering module. This embodiment allows easy cleaning of the interactive baby bottle after removing it from the covering module.

In a still further embodiment, the interactive baby bottle comprises an indicator configured to indicate the physiological state of the person (e.g. mother) bottle feeding the baby. There can be a small display unit or one or more light elements that can indicate the heart beat, breathing rate or relaxation state of the person bottle feeding the baby. As an illustrative example, the physiological state can also provide breathing guidance to the person bottle feeding the baby to get into a more coherent state (e.g. just as in relax TV) to facilitate the baby in the drinking process.

In a still further embodiment, the electronic unit is portable, the sensor unit being configured to sense the heart beat of the person carrying the electronic unit, the actuator unit being configured to remotely transmit the sensed heart beat to the baby while the baby is being bottle fed by another person. This enables remote connection between a baby and the mother. Babies can be calmed down since they recognize the mother's identical heartbeat from the gestation period. Further, the interactive baby bottle disclosed allows the mother to strengthen the bonding with the baby while bottle feeding. It also gives the father or the grandparent or any other baby feeder the opportunity to get emotionally closer to the baby during bottle feeding. The idea here is to lure the baby into believing that his/her mother is present based on hearing comforting familiar heart beat even though she is not physically present.

In a still further embodiment, the sensor unit is further configured to sense at least one body parameter of a baby while the baby is being bottle fed, the at least one body parameter of the baby being heart beat, breathing rate, body temperature, audible sensation, tactile sensation and olfactory sensation. The actuator unit is further configured to transmit the sensed body sensory signals of the baby to the person (e.g. mother) bottle feeding the baby. An indicator is configured to indicate the physiological state of the baby to the person bottle feeding the baby. This has the advantage that based on the indicated physiological state of the baby, the person (e.g. mother) bottle feeding the baby can suitably adjust his/her body parameters such as heart beat, tactile sensation to give a soothing comforting experience to the baby. This can facilitate the drinking process.

In an embodiment, plethysmograph or electrodes or ECG is disposed on a teat and is configured to sense the heart beat of the baby via the lips of the baby.

BRIEF DESCRIPTION OF THE DRAWINGS

These and other aspects, features and advantages will be further explained by the following description, by way of example only, with reference to the accompanying drawings, in which same reference numerals indicate same or similar parts, and in which:

Referring to FIG. 1, the interactive baby bottle is shown by the reference numeral 1000. The interactive baby bottle 1000 comprises:
i. a bottle portion 1200
ii. a cavity 1400
iii. a cylindrical mouth end 1600 whose external surface is threaded
iv. an internally threaded teat ring 1800
v. teat 1100

Figure 1:
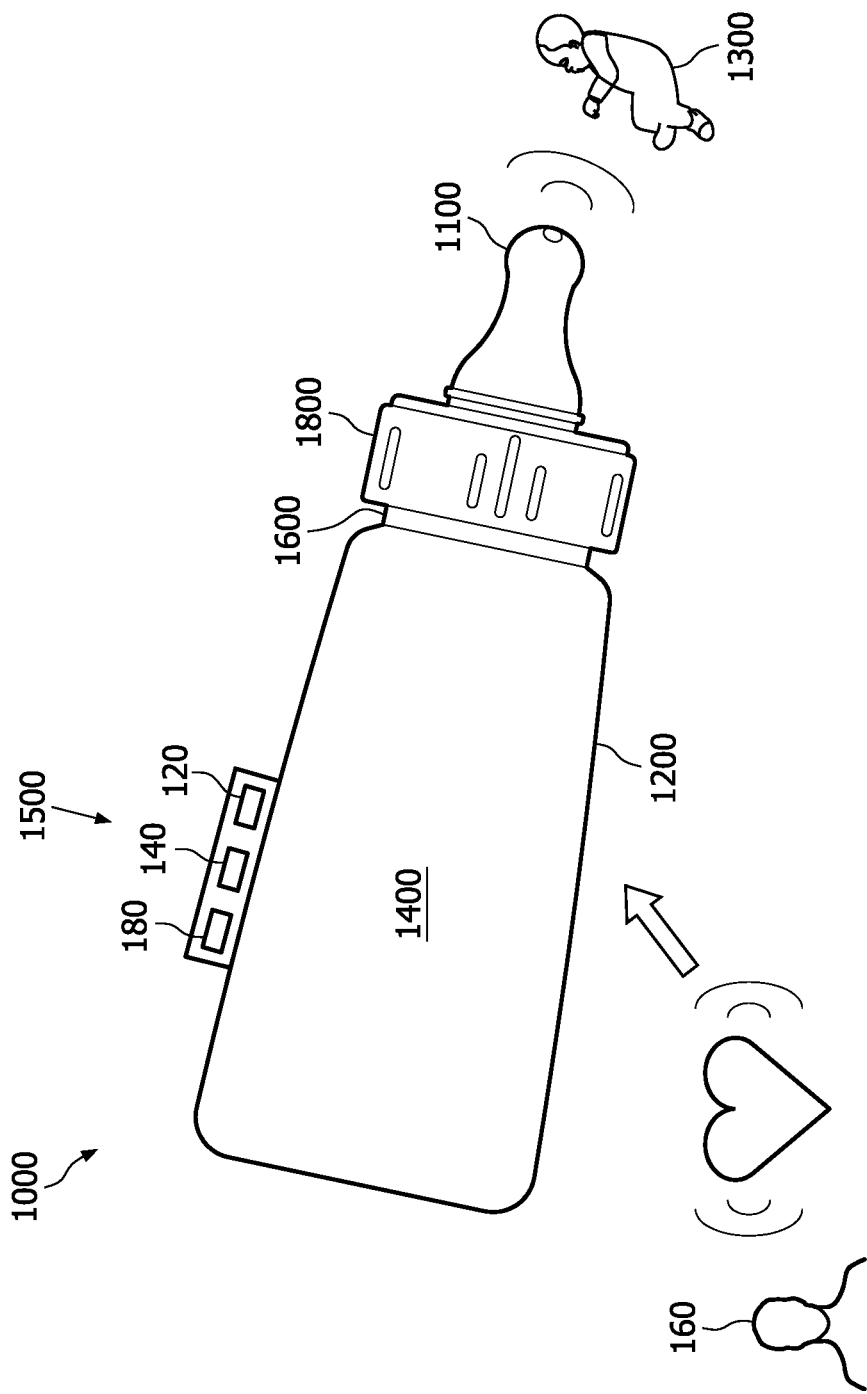
FIG. 1 schematically illustrates an exemplary interactive baby bottle according to an embodiment of the present subject matter.

The bottle portion 1200 is an elongated tube that is closed at one end and open at the other end (i.e. the mouth end). The cavity 1400 is designed to hold fluids and may include milk, formula, cereal products, water, juice and the like. The cylindrical mouth end 1600 allows fluid to flow into and out of the cavity 1400. The internally threaded teat ring 1800 engages the externally threaded cylindrical mouth end 1600 to secure the teat over the mouth end of the bottle portion 1200. It is noted here that the externally threaded mouth end and the internally threaded teat ring are described here for illustration purposes. The mouth end need not necessarily be externally threaded since it is possible to secure the teat ring on the mouth end using other methods such as a click on device. The teat is generally made of silicone rubber and contains an aperture that allows fluid contained in the cavity 1400 to pass through the teat and into the baby's mouth. Thus fluids contained in the cavity 1400 flows through the teat in a restricted manner, rather than flowing freely through the mouth end of the bottle portion.

The interactive baby bottle comprises an electronic unit 1500. The electronic unit can be integrated into the baby bottle or can be mounted within the side wall. Alternatively, the electronic unit 1500 can be a separate unit that can be fixed by a user at any convenient position on the interactive baby bottle. The electronic unit 1500 comprises:
1. a sensor unit 120
2. an actuator unit 140
3. a wireless rechargeable battery 180

The sensor unit 120 is configured to sense the heart beat of the person 160 (e.g. mother) feeding the baby 1300. The actuator unit 140 is configured to transmit the sensed heart beat to the baby.

In order to truly influence the mood-state of the baby by the bottle feeding person (e.g. mother), the baby 1300 needs to get direct feedback on the actual heart beat of the person feeding (e.g. mother) the baby. The disclosed baby bottle is interactive and is provided with an electronic unit that gives real-time feedback to the baby 1300 on the actual heart beat of the person bottle feeding (e.g. mother) the baby. The baby can feel or hear the mother's heart beat and thus can experience a sense of connectedness. Further, the disclosed interactive baby bottle can provide real-time comforting and soothing experience.

The sensed heart beat is fed back to the baby in real-time. This real-time feedback can create a higher level of bonding between the baby and the person (e.g. mother) feeding the baby. This can facilitate the drinking process.

A wirelessly rechargeable battery 180 is provided to recharge the sensor unit, the actuator unit and other components of the electronic unit. Wirelessly charging the battery has several benefits such as better portability, lower cost, no necessity to worry about carrying a charger. It is also possible to provide one or more batteries to provide power to the sensor and actuator of the electronic unit. All the components may be powered from single battery or different batteries may be included for powering one or more separate components.

Figure 2:
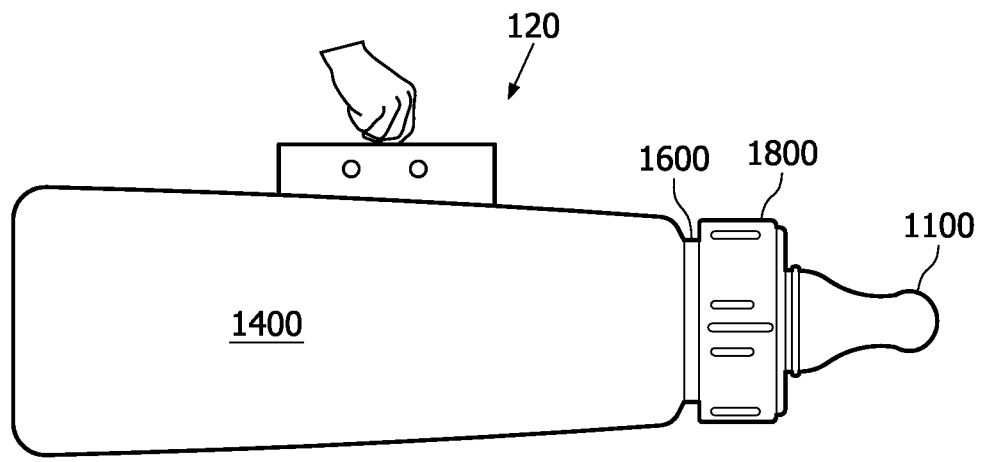
FIG. 2 schematically illustrates a sensor unit configured to sense the heart beat of the person feeding the baby according to an embodiment of the present subject matter.

Referring now to FIG. 2, the sensor unit 120 comprises one of the following: (photo) plethysmogram PPG on finger or part of the hand or the ear or other body part, SPO2 sensor, electrical electrodes measuring ECG signal, non-galvanic capacitive electrodes, acoustical sensor with microphone and any other heart rate sensor.

The sensor unit 120 can comprise a breathing rate sensor, a body movement sensor, body temperature sensor, audible sensor, tactile sensor or olfactory sensor. The actuator unit can be suitably configured to transmit the sensed sensory signal to the baby.

It is also possible to make use of any one of the following to sense the breathing rate:
motion sensors disposed on chest or belly of the person (e.g. mother) bottle feeding the baby,
stretch sensors configured to measure volume variations, the stretch sensors being disposed on chest or belly of the person (e.g. mother) bottle feeding the baby
ballistocardiogram
phonocardiogram Phonocardiogram is the measurement of the heartbeat with a microphone (e.g. a stethoscope with a microphone). Ballistocardiogram is the measurement of the heartbeat by measuring the movement of the whole body (which vibrates to the arterial arch impulse) the principles of which are disclosed in the paper "An EMFi-film sensor based ballistocardiographic chair performance and cycle extraction method", Junnila, S et.al, IEEE Workshop on Signal Processing Systems Design and Implementation, 2005, Volume, issue 2-4, pp. 373-377, Nov. 2005.

Figure 3:
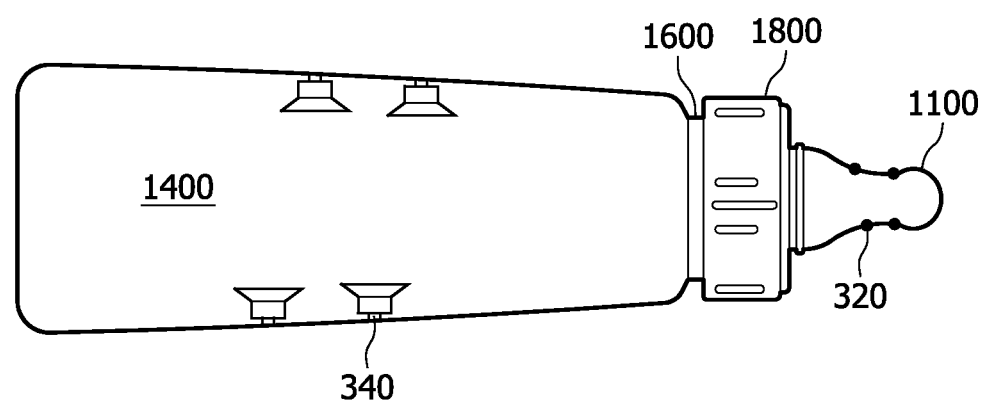
FIG. 3 schematically illustrates an actuator unit configured to transmit the sensed heart beat to the baby according to an embodiment of the present subject matter.

Referring now to FIG. 3, the actuator unit 140 comprises one of the following:
a plurality of vibration elements 320 configured to generate tactile sensation of the sensed heart beat, the vibration element 320 being integrated in the teat 1100 or being disposed suitably on the interactive baby bottle to transmit the sensed heart beat via the teat 1100 to the baby
one or more speakers 340 disposed on the interactive baby bottle and configured to provide real-time auditory feedback of the sensed heart beat to the baby.

Integrating the vibration element 320 in the teat 1100 can generate tactile sensation of the heart beat. The teat is close to the mouth of the baby as is the case during breast feeding where the mouth is close to the breast. The sensed heart beat from the teat can be more effective in creating a sense of connectedness to the person (e.g. mother) bottle feeding the baby. The vibration element 320 can be for example a motor operating an oscillating member through mechanical coupling means such as gears or a belt and pulleys.

Figure 4:
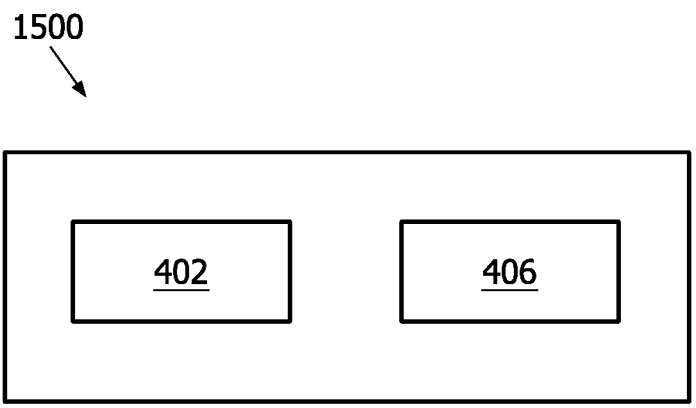
FIG. 4 schematically illustrates a further embodiment of the interactive baby bottle.

Referring now to FIG. 4, the electronic unit 1500 further comprises a memory unit 402 configured to store the sensed heart beat and a delay unit 406 configured to time-delay the sensed heart beat by a pre-determined time period and then transmit the sensed heart beat to the baby. This allows the interactive baby bottle to be designed such that it transmits the heartbeat of the person (e.g. mother) bottle feeding the baby with a certain time delay to the baby. The memory unit can store the heart beat signals from a previous time period. In case the person (e.g. mother) bottle feeding the baby becomes panic or stressed or distracted, undesired signals may be produced. It is not necessary to pass on these undesired signals to the baby. The actuator unit 140 can just repeat the more relaxed heart beat signals from the previous time period that is stored in the memory unit.

Further, the electronic unit 1500 can be integrated into the baby bottle 1000. Integrating the electronic unit into the bottle makes the interactive bottle a single piece apparatus which is convenient to carry and use. It is also possible to dispose the electronic unit on any convenient position on the interactive baby bottle. To this end, the electronic unit can be provided with a structure that allows the electronic unit to be attached in various positions. As an illustrative example, the electronic unit can be screwed (or fixed using Velcro material) onto the interactive baby bottle. In such a case a wireless interface is needed for communication with the interactive baby bottle.

In a still further embodiment, the electronic unit is integrated into the interactive baby bottle covering module. This embodiment allows easy cleaning of the interactive baby bottle after removing it from the covering module.

Figure 5:
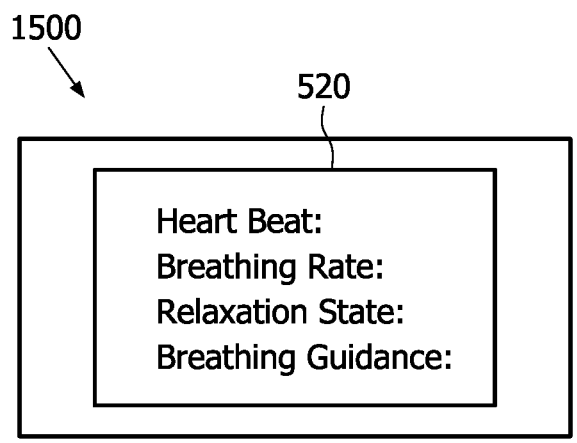
FIG. 5 schematically illustrates a still further embodiment of the interactive baby bottle.

Referring now to FIG. 5, the electronic unit 1500 further comprises an indicator 520 configured to indicate the physiological state of the person (e.g. mother) bottle feeding the baby. There can be a small display unit or one or more light elements that can indicate the heart beat, breathing rate or relaxation state of the person feeding the baby. As an illustrative example, the physiological state can also provide breathing guidance to the person bottle feeding the baby to get into a more coherent state (e.g. just as in relax TV) to facilitate the baby in the drinking process.

Figure 6:
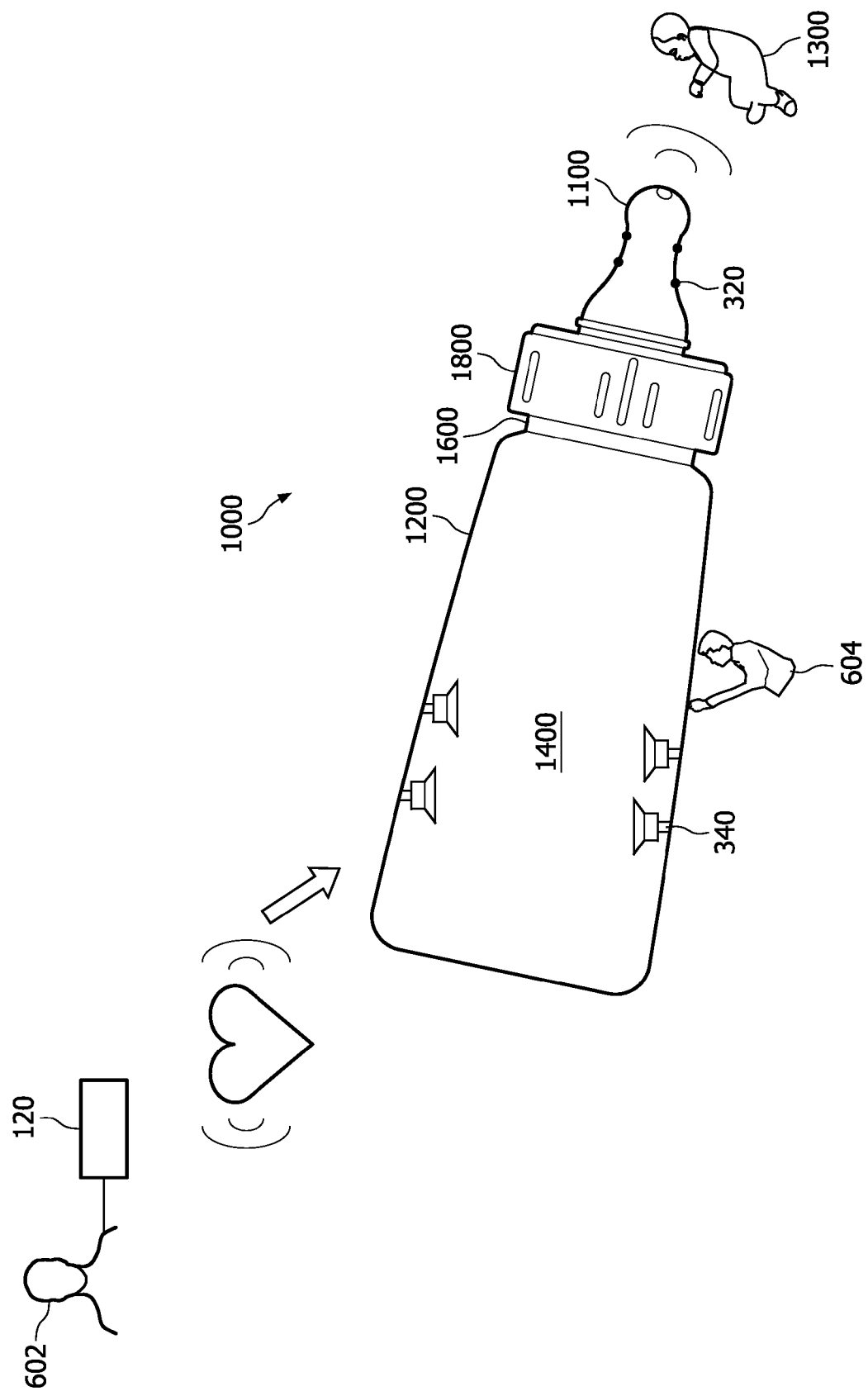
FIG. 6 schematically illustrates a still further embodiment of the interactive baby bottle wherein the electronic unit is portable.

Referring now to FIG. 6, the sensor unit 120 is portable and can be carried by a person 602. The sensor unit 120 is configured to sense the heart beat of the person 602 carrying the sensor unit 120. The sensed heart beat can be fed to the actuator unit 140. The actuator unit 140 can then transmit the sensed heart beat to the baby 1300. This enables remote connection between the baby and the mother. Babies can be calmed down since they recognize the mother's identical heartbeat from the gestation period. Further, the interactive baby bottle disclosed allows the mother to strengthen the bonding with the baby while bottle feeding. It also gives the father or the grandparent or any other baby feeder the opportunity to get emotionally closer to the baby during bottle feeding. The idea here is to lure the baby into believing that his/her mother is present based on hearing comforting familiar heart beat even though she is not physically present.

In some embodiments, the sensor unit 120 can be further configured to sense at least one body parameter of a baby while the baby is being bottle fed. The at least one body parameter of the baby can be heart beat, breathing rate, body temperature, audible sensation, tactile sensation and olfactory sensation. The actuator unit 140 can be further configured to transmit the sensed body sensory signals of the baby to the person (e.g. mother) bottle feeding the baby. The indicator 520 can be configured to indicate the physiological state of the baby to the person (e.g. mother) bottle feeding the baby. This has the advantage that based on the indicated physiological state of the baby, the person (e.g. mother) bottle feeding the baby 1300 can suitably adjust his/her body parameters such as heart beat, tactile sensation to give a soothing comforting experience to the baby. This can facilitate the drinking process.

In order to sense the heart beat of the baby, plethysmograph or electrodes or ECG can be disposed on the teat and can be configured to sense the heart beat via the lips of the baby.

In general, the prior art of designing and manufacturing a baby bottle, the sensors for sensing body signals, the actuators to transmit the sensed sensory signals can be consulted to provide examples of how to incorporate the electronic unit 1500 into the baby bottle. Further, the associated wiring, switches, timers, controllers can be incorporated into the electronic unit. Such information is generally known in the art and is not set forth in detail herein.

In summary, an interactive baby bottle with an electronic unit is disclosed. The electronic unit comprises a sensor unit configured to sense the heart beat of a person bottle feeding a baby and an actuator unit configured to transmit the sensed heart beat to the baby. The disclosed interactive baby bottle can facilitate the drinking process, since it allows bottle feeding to become an experience of connectedness between the baby and the person feeding the baby thereby approaching breast feeding.

Although claims have been formulated in this application to particular combinations of features, it should be understood that the scope of the disclosure of the present subject matter also includes any novel features or any novel combination of features disclosed herein either explicitly or implicitly or any generalization thereof, whether or not is relates to the same subject matter as presently claimed in any claim and whether or not it mitigates any or all of the same technical problems as does the present subject matter.

Further, while the subject matter has been illustrated in detail in the drawings and foregoing description, such illustration and description are to be considered illustrative or exemplary and not restrictive; the subject matter is not limited to the disclosed embodiments. Other variations to the disclosed embodiments can be understood and effected by those skilled in the art of practicing the claimed subject matter, from a study of the drawings, the disclosure and the appended claims. Use of the verb "comprise" and its conjugates does not exclude the presence of elements other than those stated in a claim or in the description. Use of the indefinite article "a" or "an" preceding an element or step does not exclude the presence of a plurality of such elements or steps. The Figures and description are to be regarded as illustrative only and do not limit the subject matter. Any reference sign in the claims should not be construed as limiting the scope.

The invention claimed is:

1. An interactive baby bottle with an electronic unit comprising:
    a sensor unit configured to sense the heart beat of a person bottle feeding a baby; and
    an actuator unit configured to transmit the sensed heart beat to the baby in real-time.

2. The interactive baby bottle as claimed in claim 1, wherein the sensor unit comprises one of the following:
    plethysmogram PPG on finger or part of the hand or the ear or other body part;
    SPO2 sensor,
    electrical electrodes measuring ECG signal,
    non-galvanic capacitive electrodes,
    acoustical sensor with microphone, and
    any other heart rate sensor.

3. The interactive baby bottle as claimed in claim 2, wherein the actuator unit comprises one of the following:
    a plurality of vibration elements configured to generate tactile sensation of the sensed heart beat, the vibration element integrated in a teat or disposed suitably on the interactive baby bottle to transmit the sensed heart beat via the teat to the baby, and
    one or more speakers disposed on the interactive baby bottle and configured to provide real-time auditory feedback of the sensed heart beat to the baby.

4. The interactive baby bottle as claimed in claim 3, further comprising:
    a memory unit configured to store the sensed heart beat; and a delay unit configured to time-delay the sensed heart beat by a pre-determined time period and then transmit the sensed heart beat to the baby.

5. The interactive baby bottle as claimed in claim 1, wherein the sensor unit is further configured to sense at least one body parameter of the person bottle feeding the baby, the at least one body parameter being one of breathing rate, body movement, body temperature, audible sensation, tactile sensation and olfactory sensation and the actuator unit further configured to transmit the sensed body parameter to the baby.

6. The interactive baby bottle as claimed in claim 5, wherein the sensor unit configured to sense the breathing rate comprises one of:
   motion sensors disposed on chest or belly of the person bottle feeding the baby,
   stretch sensors configured to measure volume variations, the stretch sensors being disposed on chest or belly of the person feeding the baby,
   ballistocardiogram, and
   phonocardiogram.

7. The interactive baby bottle as claimed in claim 1 further comprising a wirelessly rechargeable battery.

8. The interactive baby bottle as claimed in claim 1, wherein the electronic unit is integrated into the interactive baby bottle.

9. The interactive baby bottle as claimed in claim 1, wherein the electronic unit is integrated into the interactive baby bottle covering module.

10. The interactive baby bottle as claimed in claim 1, further comprising an indicator configured to indicate the physiological state of the person bottle feeding the baby.

11. The interactive baby bottle as claimed in claim 1, wherein the sensor unit is portable and detachable from the interactive baby bottle, the sensor unit being configured to sense the heart beat of a person carrying the sensor unit and feed it to the actuator unit attached to the interactive baby bottle, the actuator unit being configured to transmit the sensed heart beat of the person carrying the sensor unit to the baby while the baby is being bottle fed by another person.

12. The interactive baby bottle as claimed in claim 1, wherein the sensor unit is further configured to sense at least one body parameter of the baby while the baby is being bottle fed, the at least one body parameter of the baby being heart beat, breathing rate, body temperature, tactile sensation and olfactory sensation and the actuator unit further configured to transmit the sensed body parameter of the baby to the person bottle feeding the baby and an indicator configured to indicate the physiological state of the baby to the person bottle feeding the baby.

13. The interactive baby bottle as claimed in claim 12, wherein plethysmograph or electrodes or ECG is disposed on a teat and is configured to sense the heart beat of the baby via the lips of the baby.

* * * * *